United States Patent [19]

Yamaguchi et al.

[11] Patent Number: 5,756,306

[45] Date of Patent: May 26, 1998

[54] PROCESS FOR PRODUCING A-HYDROXY ACID OR A-HYDROXYAMIDE BY MICROORGANISM

[75] Inventors: Yasumasa Yamaguchi; Masahiro Ushigome; Takeshi Kato, all of Kanagawa, Japan

[73] Assignee: Nitto Chemical Industry Co., Ltd., Tokyo, Japan

[21] Appl. No.: 745,918

[22] Filed: Nov. 8, 1996

[30] Foreign Application Priority Data

Nov. 10, 1995 [JP] Japan .................... 7-315806
Nov. 10, 1995 [JP] Japan .................... 7-315807

[51] Int. Cl.$^6$ ................... C12P 1/04; C12P 7/42; C07C 29/14; C07C 51/08

[52] U.S. Cl. ................... 435/41; 435/129; 435/132; 435/155; 558/303; 558/451; 564/473; 564/490; 568/700; 568/704; 568/880; 562/531; 423/364

[58] Field of Search ................... 435/41, 129, 132, 435/155

[56] References Cited

U.S. PATENT DOCUMENTS 5,326,702  7/1994  Endo et al. .................... 435/129

FOREIGN PATENT DOCUMENTS 0 711 836 A1  5/1996  European Pat. Off. .......... C12P 7/42

*Primary Examiner*—Johann Richter
*Assistant Examiner*—Jane C. Osowecki
*Attorney, Agent, or Firm*—Sughrue, Mion, Zinn, Macpeak & Seas, PLLC

[57] ABSTRACT

A process for producing an α-hydroxy acid or an α-hydroxyamide which comprises treating an aldehyde and prussic acid or an α-hydroxynitrile with a microorganism having nitrilase or nitrile hydratase activity in an aqueous medium and maintaining the aldehyde concentration and/or the α-hydroxynitrile concentration in the reaction mixture within a predetermined range. Also disclosed is a process for producing an α-hydroxy acid or an α-hydroxyamide from an aldehyde and prussic acid with a microorganism in an aqueous medium, which comprises maintaining the cyanogen concentration in the reaction mixture within a predetermined range and supplying the aldehyde to the reaction mixture at a predetermined ratio to the prussic acid.

15 Claims, No Drawings

PROCESS FOR PRODUCING A-HYDROXY ACID OR A-HYDROXYAMIDE BY MICROORGANISM

FIELD OF THE INVENTION

This invention relates to a process for producing an α-hydroxy acid or an α-hydroxyamide by a microorganism. In particular, optically active α-hydroxyamides and α-hydroxy acids are industrially valuable as starting materials for synthesizing various drugs, agricultural chemicals, etc.

BACKGROUND OF THE INVENTION

Examples of known processes for producing α-hydroxy acids by microorganisms include those which use microorganisms belonging to the genera Alcaligenes, Pseudomonas, Rhodopseudomonas, Corynebacterium, Acinetobacter, Bacillus, Mycobacterium, Rhodococcus, Candida, Nocardia, etc. (JP-A-2-84198, JP-A-3-224496, JP-A-3-277292, etc.; the term "JP-A" as used herein means an "unexamined published Japanese patent application") and those which use microorganisms belonging to the genera Nocardia, Bacillus, Brevibacterium, Aureo-bacterium, Pseudomonas, Caseobacter, Alcaligenes, Acineto-bacter, Enterobacter, Arthrobacter, Escherichia, Micrococcus, Streptomyces, Flavobacterium, Aeromonas, Mycoplana, Cellulomonas, Erwinia, Candida, Bacteridium, Aspergillus, Penicillium, Cochliobolus, Fusarium, Rhodopseudomonas, Rhodococcus, Corynebacterium, Microbacterium, Obsumbacterium, Gordona, etc. (JP-A-4-99495, JP-A-4-99496 and JP-A-4-218385 corresponding to U.S. Pat. No. 5,223,416; JP-A-4-99497 corresponding to U.S. Pat. No. 5,234,826; JP-A-5-95795 corresponding to U.S. Pat. No. 5,296,373; JP-A-5-21987; JP-A-5-192189 corresponding to U.S. Pat. No. 5,326,702; JP-A-6-237789 corresponding to EP-A-0610048; JP-A-6-284899 corresponding to EP-A-0610049; JP-A-7-213296 corresponding to U.S. Pat. No. 5,508,181; etc.).

On the other hand, examples of known processes for producing α-hydroxyamides by microorganisms include those which use microorganisms belonging to the genera Rhodococcus, Corynebacterium, Pseudomonas, Arthrobacter, Alcaligenes, Bacillus, Bacteridium, Micrococcus, Brevibacterium, Nocardia, etc. (JP-A-4-222591; JP-A-5-192189 corresponding to U.S. Pat. No. 5,326,702; JP-A-7-213296 corresponding to U.S. Pat. No. 5,508,181; etc.).

When an α-hydroxynitrile is enzymatically hydrolyzed or hydrated using nitrilase or nitrile hydratase to produce an α-hydroxy acid or an α-hydroxyamide, a problem occurs in that the enzyme is inactivated within a short period of time. It is therefore difficult to obtain the α-hydroxy acid or α-hydroxyamide in high concentration and high yield.

When an aldehyde and prussic acid, which are economically preferred to α-hydroxynitrile, are employed as the starting materials, another problem occurs in that the reaction rate is lowered with an increase in the concentration of the α-hydroxy acid or α-hydroxyamide product in the reaction mixture. As a result, the reaction does not proceed to completion.

The present inventors have conducted extensive studies in order to solve these problems. As a result, the present inventors discovered that enzyme inactivation can be suppressed when an α-hydroxy acid or α-hydroxyamide represented by the following formula (3) is produced from a corresponding aldehyde represented by the following formula (1) and prussic acid or a corresponding α-hydroxynitrile represented by the following formula (2) by measuring the aldehyde concentration and/or the α-hydroxynitrile concentration in the reaction mixture and by maintaining the aldehyde concentration and/or the α-hydroxynitrile concentration in the reaction system within a predetermined range. Thus, α-hydroxy acid or α-hydroxyamide in high concentration can be produced in high yield. The present inventors furthermore discovered that enzyme inactivation can be suppressed when an α-hydroxy acid or an α-hydroxyamide represented by the following formula (3) is produced from a corresponding aldehyde represented by the following formula (1) and prussic acid by measuring the cyanogen concentration in the reaction mixture and by supplying prussic acid to the reaction mixture in such manner so as to maintain the cyanogen concentration within a predetermined range and by supplying the aldehyde to the reaction mixture at a predetermined ratio to the prussic acid. Thus, α-hydroxy acid or α-hydroxyamide can be produced in high concentration and in high yield. The present invention has been completed based on these findings.

SUMMARY OF THE INVENTION

Accordingly, the present invention provides a process for producing an α-hydroxy acid or an α-hydroxyamide which comprises treating an aldehyde represented by the following formula (1) and prussic acid or an α-hydroxynitrile represented by the following formula (2) with a microorganism or processed product thereof having nitrilase or nitrile hydratase activity in an aqueous medium to thereby provide a reaction mixture containing a corresponding α-hydroxy acid or α-hydroxyamide represented by the following formula (3), and maintaining the aldehyde concentration and/or the α-hydroxynitrile concentration in the reaction mixture within a predetermined range. In a preferred embodiment, the invention further comprises measuring the aldehyde concentration and/or the α-hydroxynitrile concentration in the reaction mixture, and continuously and/or intermittently supplying the aldehyde and prussic acid or the α-hydroxynitrile to the reaction mixture in such manner so as to maintain at least one of the aldehyde concentration and the α-hydroxynitrile concentration within a predetermined range. The present invention also provides a process for producing an α-hydroxy acid or an α-hydroxyamide represented by the following formula (3) from an aldehyde represented by the above formula (1) and prussic acid with a microorganism or processed product thereof having nitrilase or nitrile hydratase activity in an aqueous medium, which comprises maintaining the cyanogen concentration in the reaction mixture within a predetermined range, and supplying the aldehyde to the reaction mixture in an amount of from 0.98 to 1.05 mol per mol of prussic acid. In a preferred embodiment, the invention further comprises measuring the cyanogen concentration in the reaction mixture and continuously and/or intermittently supplying prussic acid in such manner so as to maintain the cyanogen concentration within a predetermined range.

Formulae (1) to (3) are defined below:

$$R-CHO \qquad (1)$$

-continued

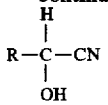

wherein R represents a substituted or unsubstituted alkyl group, a substituted or unsubstituted alkenyl group, a substituted or unsubstituted cycloalkyl group, a substituted or unsubstituted aryl group, or a substituted or unsubstituted, saturated or unsaturated heterocyclic group; and X represents an amido group or a carboxyl group.

DETAILED DESCRIPTION OF THE INVENTION

In the present invention, the aldehyde, prussic acid, α-hydroxynitrile and sulfite ion, which sulfite ion is added if needed, are in an equilibrium state and react with each other in the reaction mixture. Thus it is difficult to determine the actual concentrations of these substances. Accordingly, the apparent concentration(s) of the aldehyde and/or α-hydroxynitrile in the reaction mixture are determined. More particularly, the reaction mixture during the course of the reaction is sampled and, if necessary, diluted and subjected to solid-liquid separation followed by an analysis of the solution thus obtained. Although it is preferable to employ liquid chromatography for this analysis, gas chromatography can also be used. The aldehyde or α-hydroxynitrile is supplied to the reaction mixture in such manner so as to regulate (control) the aldehyde concentration and/or the α-hydroxynitrile concentration in the reaction mixture generally within a concentration range of from 0.01 to 1,000 mM, preferably from 0.05 to 200 mM, and still preferably from 1 to 50 mM. In the last step of the reaction, the supply of the aldehyde or α-hydroxynitrile is discontinued to thereby lower the aldehyde concentration and/or the α-hydroxynitrile concentration in the reaction mixture.

When an aldehyde and prussic acid are employed as starting materials, it is also possible to measure the cyan ion concentration to thereby control the supply of the prussic acid and aldehyde. The concentration of cyanogen in the reaction mixture can be determined using a cyan ion sensor, an infrared gas analyzer, a semiconductor gas sensor, etc. Prussic acid is supplied to the reaction mixture in such manner so as to control the cyanogen concentration in the reaction mixture within a predetermined range, generally from 0.01 to 300 mM, preferably from 0.1 to 100 mM, and still preferably from 1 to 50 mM. In the present invention, the expression "cyanogen concentration in the reaction mixture" means the sum of the concentrations of prussic acid and cyan ion contained therein. Furthermore, the aldehyde is supplied to the reaction mixture at a ratio of from 0.98 to 1.05 mol, preferably from 0.99 to 1.03 mol, per mol of prussic acid. In the last step of the reaction, the supply of the aldehyde is discontinued, and prussic acid is supplied alone if necessary so as to lower the concentration of the aldehyde in the reaction mixture.

As used and claimed herein, it is to be understood that "supplying prussic acid to the reaction mixture" includes supplying a cyanide salt or solution thereof to the reactor such as a sodium cyanide solution.

When the cyanogen concentration in the reaction mixture is determined using a cyan ion sensor, the short life of the cyanogen sensor can be prolonged by diluting the reaction mixture with an aqueous medium. When an infrared gas analyzer or a semiconductor gas sensor is employed therefor, this measurement can be carried out by determining the prussic acid gas concentration in the gas which contacts the reaction mixture.

In general, aldehydes bind to proteins and thus inactivate enzymes. Therefore, the present inventors expect that the method of regulating the effect of inhibiting an enzyme, which comprises measuring the aldehyde concentration and/or the α-hydroxynitrile concentration or the cyanogen concentration in the reaction mixture and controlling the aldehyde concentration and/or the α-hydroxynitrile concentration in the reaction mixture to within a predetermined range, is applicable as a rule to all microbial reactions in which aldehydes participate. Therefore, the microorganism for use in the process of the present invention for producing an acid or an amide from an aldehyde, prussic acid and α-hydroxynitrile is not particularly limited, so long as it is capable of forming the acid or amide (i.e., having nitrilase or nitrile hydratase activity).

Examples of microorganisms which are useful in the present invention include those belonging to the genera Pseudomonas, Alcaligenes, Acinetobacter, Caseobacter, Corynebacterium, Brevibacterium, Nocardia, Rhodococcus, Gordona, Arthrobacter, Bacillus, Aureobacterium, Enterobacter, Escherichia, Micrcoccus, Streptomyces, Flavobacterium, Aeromonas, Mycoplana, Cellulomonas, Erwinia, Candida, Bacteridium, Aspergillus, Penicillium, Cochliobolus, Fusarium, Rhodopseudomonas, etc.

More particularly, for example, the following microorganisms are useful in the present invention.

*Pseudomonas sp.* BC13-2 (FERM BP-3319); BC15-2 (FERM BP-3320), SK13 (FERM BP-3325), SK31 (FERM P-11310) and SK87 (FERM P-11311), *Pseudomonas synxanta* IAM 12356, *Alcaligenes sp.* BC12-2 (FERM P-11263), BC20 (FERM P-11264) and BC35-2 (FERM BP-3318), *Acinetobacter sp.* BC9-2 (FERM BP-3317), *Caseobacter sp.* BC4 (FERM BP-3316) and BC23 (FERM P-11261), *Corynebacterium nitrilophilus* ATCC 21419, *Brevibacterium acetylicum* IAM 1790, *Brevibacterium helvolum* ATCC 11822, *Nocardia sp.* N-775 (FERM P-4447), *Nocardia asteroides* IFO 3384, *Nocardia calcarea* KCCA 0191, *Nocardia polychromogenes* IFM 19, *Rhodococcus sp.* SK70 (FERM P-11304), SK92 (FERM BP-3324) and HR11 (FERM P-11306), *Rhodococcus rhodochrous* ATCC 12674, ATCC 19140 and ATCC 33258, *Rhodococcus erythropolis* IFM 155, IFO 12320, IFO 12538 and IFO 12540, *Gordona terrae*, MA-1 (FERM BP-4535) *Arthrobacter sp.* SK103 (FERM P-11300), HR1 (FERM BP-3323) and HR4 (FERM P-11302), *Arthrobacter oxydans* IFO 12138, *Bacillus subtilis* ATCC 21697, *Bacillus licheniformis* IFO 12197, *Bacillus megaterium* ATCC 25833, *Aureobacterium testaceum* IAM 1561, *Enterobacter sp.* SK12 (FERM BP-3322), *Escherichia coli* IFO 3301, *Micrococcus luteus* ATCC 383, *Micrcoccus varians* IAM 1099, *Micrococcus roseus* IFO 3768, *Streptomyces griseus* IFO 3355, *Flavobacterium sp.* SK150 (FERM P-11645), *Flavobacterium flavescens* ATCC 8315, *Aeromonas punctata* IFO 13288, *Mycoplana dimorpha* ATCC 4297, *Cellulomonas fimi* IAM 12107, *Erwinia herbicola* IFO 12686 and *Candida guilliermondii* IFO 0566.

These microorganisms are respectively described in the above-cited patent publications.

On the other hand, examples of useful microorganisms in the present invention having nitrile hydratase activity include those belonging to the genera Rhodococcus, Corynebacterium, Pseudomonas, Arthrobacter, Alcaligenes, Bacillus, Bacteridium, Micrococcus, Brevibacterium and Nocardia.

More particularly, for example, the following microorganisms are useful in the present invention.

*Rhodococcus sp.* HT40-6 (FERM BP-5231), *Rhodococcus rhodochrous* ATCC 33278, *Rhodococcus erythropolis* IFO 12320, *Corynebacterium nitrilophilus* ATCC 21419, *Pseudomonas sp.* SK87 (FERM P-11311), *Arthrobacter sp.* HR1 (FERM BP-3323) and *Alcaligenes sp.* BC16-2 (FERM BP-3321).

These microorganisms are respectively described in the above-cited patent publications.

The aldehyde represented by formula (1) and the α-hydroxynitrile represented by the formula (2) for use in the present invention are those wherein R represents a substituted or unsubstituted alkyl (e.g., $C_1$–$C_6$ alkyl) group, a substituted or unsubstituted alkenyl (e.g., $C_2$–$C_3$ alkenyl) group, a substituted or unsubstituted cycloalkyl (e.g., cyclohexyl) group, a substituted or unsubstituted aryl group (e.g., phenyl), or a substituted or unsubstituted, saturated or unsaturated heterocyclic (e.g., one ring) group. In the reaction mixture, the aldehyde, prussic acid and α-hydroxynitrile are in a dissociated equilibrium state.

Useful heterocyclic groups represented by R contain at least one heteroatom selected from among nitrogen, oxygen and sulfur atoms.

Examples of useful substituents for the substituted group represented by R include alkyl, alkoxy, acyl, aryl and aryloxy groups, halogen atoms such as chlorine and bromine atoms and hydroxyl, amino, nitro and thiol groups.

Particular examples of the aldehyde include acetaldehyde, propionaldehyde, n-butylaldehyde, n-pentylaldehyde, n-hexylaldehyde, n-heptylaldehyde, β-hydroxy-α,α-dimethylpropionaldehyde, acrolein, 3-phenylacrolein, methacrylaldehyde, 2-chloroacetaldehyde, 3-methylthiopropionaldehyde and 2-phenylaldehyde which are optionally substituted. Furthermore, aromatic aldehydes and those having heterocyclic rings can also be used such as benzaldehyde, 2-thiophenaldehyde, 2-pyridinaldehyde, 2-pyrrolaldehyde and 2-furaldehyde which are optionally substituted. As for the prussic acid, a cyanide such as sodium cyanide or potassium cyanide can be used.

Examples of the α-hydroxynitrile include lactonitrile, α-hydroxy-butyronitrile, α-hydroxy-n-pentylonitrile, α-hydroxy-n-hexylonitrile, α-hydroxy-n-heptylonitrile, α-hydroxy-n-octylonitrile, α,γ-dihydroxy-β,β-dimethylbutyronitrile, acrolein cyanohydrin, 3-phenylacrolein cyanohydrin, methacrylaldehyde cyanohydrin, 3-chlorolactonitrile, 4-methylthio-α-hydroxybutyronitrile and α-hydroxy-α-phenylpropionyl which are optionally substituted. Furthermore, aromatic α-hydroxynitriles and those having heterocyclic rings can also be used such as mandelonitrile, 2-thiophenaldehyde cyanohydrin, 2-pyridinaldehyde cyanohydrin, 2-pyrrolaldehyde cyanohydrin and 2-furaldehyde cyanohydrin which are optionally substituted.

Enzyme inhibition by the aldehyde is effectively suppressed by adding sulfite ion such as a sulfurous acid salt or an acidic sulfurous acid salt. Examples of the salt include sodium, potassium and ammonium salts. The salt may be added in an amount of from 1 to 1,000 mM to the reaction mixture.

When a microorganism having a stereospecific nitrilase or nitrile hydratase or a processed product thereof (e.g., enzyme, immobilized enzyme, immobilized cell) is employed in the reaction, it is possible to convert at least 50% of the α-hydroxy acid or α-hydroxyamide product (i.e., at least 50% of the starting material) into one of the optically active substances. Thus, an optically active α-hydroxy acid or α-hydroxyamide can be advantageously obtained without having to optically resolve the product.

DESCRIPTION OF THE PREFERRED EMBODIMENTS

The hydrolysis or hydration is performed by contacting a mixture of the aldehyde represented by formula (1) and prussic acid, or the α-hydroxynitrile represented by formula (2) with a microorganism or a processed product thereof (e.g., ground cell, crude enzyme, purified enzyme, immobilized cell, immobilized enzyme) in an aqueous medium such as water or a buffer.

In the present invention, the aldehyde concentration and/or the α-hydroxynitrile concentration or the cyanogen concentration in the reaction mixture are measured in this step, and the aldehyde and prussic acid or the α-hydroxynitrile are continuously and/or intermittently added thereto so as to maintain the concentrations thereof within a predetermined range.

The aldehyde concentration and/or the α-hydroxynitrile concentration in the reaction mixture are as defined above. The microorganism is employed in an amount of from 0.001 to 5.0% by weight on a dry basis based on the substrate. The reaction temperature generally ranges from the freezing point to 50° C., preferably from 5° to 30° C.

When the α-hydroxynitrile or aldehyde has an extremely low solubility in the aqueous medium, the reaction can be efficiently carried out by adding 0.1 to 5.0% by weight of a surfactant (Triton X-100, Tween 60, etc.), methanol, ethanol, dimethyl sulfoxide, etc.

The α-hydroxy acid or α-hydroxyamide thus obtained may be isolated by treating the reaction mixture, from which insoluble matter including the cells has been removed, by procedures well known to those of ordinary skill such as concentration, ion exchange, electrodialysis, extraction, crystallization, etc.

To further illustrate the present invention in greater detail, and not by way of limitation, the following Examples are given below.

EXAMPLE 1

A 50 mM phosphate buffer (pH 8.0) containing 1,000 mM of sodium sulfite was charged into a reactor and the temperature was adjusted to 30° C. Then *Gordona terrae* MA-1 strain was suspended in this solution so as to obtain an $OD_{630}$ of 4.2. Then, an aqueous solution of sodium cyanide and benzaldehyde as starting materials were supplied to the reactor while controlling the molar ratio thereof to 1.0:1.0. The cyan ion concentration in the reaction mixture was measured with a cyan ion detector, and the supply rate of the aqueous solution of sodium cyanide was controlled so as to adjust the output of the cyan ion detector to within −220 to −224 mV. In the course of the reaction, the reaction mixture was sampled and filtered. The filtrate was diluted 10-fold with water and the benzaldehyde concentration was measured by liquid chromatography. Thus, the supply rates of the aqueous solution of sodium cyanide and benzaldehyde were regulated to maintain the benzaldehyde concentration in the reaction mixture within the range of from 10 to 15 mM.

After carrying out the reaction for 22 hours, the reacted mixture contained R-mandelic acid in a concentration of 10.5% and an optical purity of 99.0% ee. The R-mandelic acid concentration and optical purity were determined by liquid chromatography. The yield of the R-mandelic acid based on the benzaldehyde supplied to the reactor was 97.0%.

EXAMPLE 2

The procedure of Example 1 was repeated except for substituting the aqueous solution of sodium cyanide by prussic acid. After carrying out the reaction for 22 hours, the reacted mixture contained R-mandelic acid in a concentration of 14.2% and an optical purity of 99.0% ee. The yield of the R-mandelic acid based on the benzaldehyde supplied to the reactor was 97.0%.

EXAMPLE 3

A 20 mM phosphate buffer (pH 8.5) was charged to a reactor and the temperature was adjusted to 10° C. Then, *Rhodococcus sp.* HT40-6 strain was suspended in this solution so to provide an $OD_{630}$ of 4.2.

After adding benzaldehyde to the reactor and dissolving the same to provide a concentration of 30 mM, benzaldehyde and prussic acid as starting materials were supplied to the reactor in a molar ratio thereof to 1.0:1.0. The cyan ion concentration in the reaction mixture was measured with a cyan ion detector, and the supply rate of the aqueous solution of sodium cyanide was controlled so as to adjust the output of the cyan ion detector to within −145 to −150 mV. During the course of the reaction, the reaction mixture was sampled and filtered. The filtrate was diluted 10-fold with water and the benzaldehyde concentration was measured by liquid chromatography. Thus, the supply rates of the aqueous solution of sodium cyanide and benzaldehyde were regulated to thereby maintain the benzaldehyde concentration in the reaction mixture within the range of from 35 to 40 mM.

After carrying out the reaction for 66 hours, the reacted mixture contained mandelamide in a concentration of 32% and an optical purity (S-mandelamide) of 77% ee. The yield of the mandelamide based on the benzaldehyde supplied to the reactor was 95%. Mandelamide was crystallized from the reacted mixture.

EXAMPLE 4

A 50 mM phosphate buffer (pH 8.0) containing 100 mM of sodium sulfite was charged to a reactor and the temperature was adjusted to 30° C. Then *Gordona terrae* MA-1 strain was suspended in this solution so as to provide an $OD_{630}$ of 4.2. Then, mandelonitrile employed as a starting material was supplied to the reactor at a predetermined rate. During the course of the reaction, the reaction mixture was sampled and filtered. The filtrate was diluted 10-fold with water and the benzaldehyde concentration was measured by liquid chromatography. Thus, the flow rate of the mandelonitrile was regulated to thereby maintain the benzaldehyde concentration in the reaction mixture within the range of from 10 to 15 mM.

After carrying out the reaction for 22 hours, the reacted mixture contained R-mandelic acid in a concentration of 12.5% and an optical purity of 77% ee. The yield of the R-mandelic acid based on the benzaldehyde supplied to the reactor was 95%.

Comparative Example 1

A 50 mM phosphate buffer (pH 8.0) containing 100 mM of sodium sulfite was charged to a reactor and the temperature was adjusted to 30° C. Then *Gordona terrae* MA-1 strain was suspended in this solution so as to provide an $OD_{630}$ of 4.2. Then, an aqueous solution of sodium cyanide and benzaldehyde as starting materials were supplied in a molar ratio of 1.0:1.0. The cyan ion concentration in the reaction mixture was measured with a cyan ion detector, and the supply rate of the aqueous solution of sodium cyanide was controlled so as to adjust the output of the cyan ion detector to within −220 to −224 mV.

After carrying out the reaction for 22 hours, the reacted mixture contained R-mandelic acid in a concentration of 5.0% and an optical purity of 97% ee. The yield of the R-mandelic acid based on the benzaldehyde supplied to the reactor was 93%.

EXAMPLE 5

A 50 mM phosphate buffer (pH 8.0) containing 100 mM of sodium sulfite was charged to a reactor and the temperature was adjusted to 30° C. Then, *Gordona terrae* MA-1 strain was suspended in this solution so as to provide an $OD_{630}$ of 4.2. Then, an aqueous solution of sodium cyanide and benzaldehyde employed as starting materials were supplied in a molar ratio of 1.0:0.98. The cyan ion concentration in the reaction mixture was measured with a cyan ion detector, and the supply rate of the aqueous solution of sodium cyanide was controlled so as to adjust the output of the cyan ion detector to within −220 to −224 mV. In this case, the cyanogen concentration in the reaction mixture was regulated within the range of from 20 to 22 mM.

After carrying out the reaction for 22 hours, the supply of benzaldehyde was discontinued while the supply of the aqueous solution of sodium cyanide was continued. Table 1 shows the results of the reaction performed for 30 hours.

EXAMPLES 6 TO 10

The procedure of Example 5 was repeated except for controlling the molar ratio of the aqueous solution of sodium cyanide and benzaldehyde starting materials as specified in Table 1. Table 1 shows the results of the reaction performed for 30 hours.

EXAMPLE 11

The procedure of Example 5 was repeated except for substituting prussic acid for the aqueous solution of sodium cyanide acid and controlling the molar ratio of prussic acid to benzaldehyde to 1.00:1.00. After carrying out the reaction for 30 hours, the reacted mixture contained R-mandelic acid in a concentration of 14.5% and an optical purity of 99.0% ee. The yield of the R-mandelic acid based on the benzaldehyde supplied to the reactor was 97.8%.

EXAMPLE 12

A 20 mM phosphate buffer (pH 8.5) was charged to a reactor and the temperature was adjusted to 10° C. Then, *Rhodococcus sp.* HT40-6 strain was suspended in this solution so as to provide an $OD_{630}$ of 4.2.

After adding benzaldehyde thereto and dissolving the same so as to provide a concentration of 30 mM, prussic acid and benzaldehyde starting materials were supplied to the reactor while controlling the molar ratio thereof to 1.0:1.02. The cyan ion concentration in the reaction mixture was measured with a cyan ion detector, and the supply rate of the aqueous solution of sodium cyanide was controlled so as to adjust the output of the cyan ion detector to within −145 to −150 mV. In this case, the cyanogen concentration in the reaction mixture was controlled to within the range of from 18 to 20 mM. After carrying out the reaction for 66 hours, the reacted mixture contained mandelamide in a concentration of 33% and an optical purity (S-mandelamide) of 77% ee. The yield of the mandelamide based on the benzaldehyde supplied to the reactor was 95%. Mandelamide was crystallized from the reacted mixture.

Comparative Example 2

A 50 mM phosphate buffer (pH 8.0) containing 100 mM of sodium sulfite was charged to a reactor and the temperature was adjusted to 30° C. Then *Gordona terrae* MA-1 strain was suspended in this solution so as to provide an $OD_{630}$ of 4.2. Then, an aqueous solution of sodium cyanide and benzaldehyde starting materials were supplied in a molar ratio thereof to 1.0:0.97. The cyan ion concentration in the reaction mixture was measured with a cyan ion detector, and the supply rate of the aqueous solution of sodium cyanide was controlled so as to adjust the output of the cyan ion detector to within −220 to −224 mV. After carrying out the reaction for 22 hours, the supply of the benzaldehyde was discontinued while the supply of the aqueous solution of sodium cyanide was continued. Table 1 shows the results of the reaction performed for 30 hours.

Comparative Example 3

The procedure of Comparative Example 2 was repeated, except for controlling the molar ratio of the aqueous solution of sodium cyanide and benzaldehyde employed as starting materials to 1.00:1.06. Table 1 shows the results of the reaction performed for 30 hours.

or processed product thereof in an aqueous medium to thereby provide a reaction mixture containing the corresponding α-hydroxy acid or α-hydroxyamide represented by the following formula (3), and maintaining at least one of the aldehyde concentration and the α-hydroxynitrile concentration in the reaction mixture within a range of from 0.01 to 1000 mM:

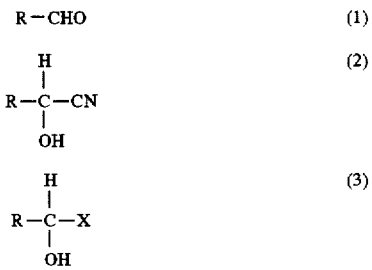

wherein R represents a substituted or unsubstituted alkyl group, a substituted or unsubstituted alkenyl group, a substituted or unsubstituted cycloalkyl group, a substituted or unsubstituted aryl group, or a substituted or unsaturated, saturated or unsaturated heterocyclic group; and X represents an amido group or carboxyl groups wherein said processed product comprises one of a ground cell, a crude enzyme, a purified enzyme, an immobilized cell or an immobilized enzyme.

2. A process for producing an α-hydroxy acid or an α-hydroxyamide by a microorganism or processed product thereof as claimed in claim 1, which comprises measuring at least one of the aldehyde concentration and the α-hydroxynitrile concentration in the reaction mixture by liquid chromatography.

TABLE 1

| Ex. No. | Sodium Cyanide (mol. ratio) | Benzaldehyde (mol. ratio) | Accumulated Concentration (%) | Optical Purity (%) | Mandelic Acid Yield (%) | R-mandelic Acid Yield (%) |
|---|---|---|---|---|---|---|
| Ex. 5 | 1.00 | 0.98 | 9.5 | 94.8 | 99.9 | 94.7 |
| Ex. 6 | 1.00 | 0.99 | 10.2 | 95.9 | 99.7 | 95.6 |
| Ex. 7 | 1.00 | 1.00 | 10.6 | 96.5 | 97.7 | 94.3 |
| Ex. 8 | 1.00 | 1.02 | 10.1 | 98.3 | 96.7 | 94.3 |
| Ex. 9 | 1.00 | 1.04 | 9.9 | 98.5 | 94.6 | 93.2 |
| Ex. 10 | 1.00 | 1.05 | 9.7 | 98.5 | 93.7 | 92.3 |
| C. Ex. 2 | 1.00 | 0.97 | 6.0 | 93.0 | 99.9 | 93.9 |
| C. Ex. 3 | 1.00 | 1.06 | 9.3 | 98.7 | 91.0 | 89.8 |

In accordance with the present invention, an α-hydroxynitrile can be hydrolyzed or hydrated while maintaining the aldehyde concentration, which is one of the factors inhibiting the enzyme, at a continuously low level during the reaction. Thus, the enzymatic activity can be sustained in a stable state for a prolonged period of time. This makes it possible to accumulate the acid or amide product in a high concentration.

While the invention has been described in detail and with reference to specific embodiments thereof, it will be apparent to one skilled in the art that various changes and modifications can be made therein without departing from the spirit and scope thereof.

What is claimed is:

1. A process for producing an α-hydroxy acid or an α-hydroxyamide by a microorganism or processed product thereof having nitrilase or nitrile hydratase activity, which comprises treating an aldehyde represented by the following formula (1) and prussic acid or an α-hydroxynitrile represented by the following formula (2) with the microorganism 3. A process for producing an α-hydroxy acid or an α-hydroxyamide as claimed in claim 1, which further comprises measuring at least one of the aldehyde concentration and the α-hydroxynitrile concentration in said reaction mixture and continuously or intermittently supplying the aldehyde and prussic acid or the α-hydroxynitrile to the reaction mixture in such manner so as to maintain at least one of the aldehyde concentration and the α-hydroxynitrile concentration in the reaction mixture within a range of from 0.01 to 1000 mM.

4. The process for producing an α-hydroxy acid or an α-hydroxyamide as claimed in claim 3, wherein said supplying step comprises supplying an aqueous cyanide salt solution to the reaction mixture and regulating the supply rates of the aldehyde and the aqueous cyanide salt solution to the reaction mixture so as to maintain at least one of the aldehyde concentration and the α-hydroxynitrile concentration within a range of from 0.01 to 100 mM.

5. The process for producing an α-hydroxy acid or an α-hydroxyamide as claimed in claim 3, wherein said supplying step comprises regulating the supply rate of the α-hydroxynitrile to the reaction mixture so as to maintain at least one of the aldehyde concentration and the α-hydroxynitrile concentration in the reaction mixture within a range of from 0.01 to 100 mM.

6. The process for producing an α-hydroxy acid or an α-hydroxyamide as claimed in claim 1, which comprises maintaining at least one of the aldehyde concentration and the α-hydroxynitrile concentration in the reaction mixture within a range of from 0.05 to 200 mM.

7. The process for producing an α-hydroxy acid or an α-hydroxyamide as claimed in claim 1, which comprises maintaining at least one of the aldehyde concentration and the α-hydroxynitrile concentration in the reaction mixture within a range of from 1 to 50 mM.

8. The process for producing an α-hydroxy acid or an α-hydroxyamide as claimed in claim 1, which comprises maintaining the aldehyde concentration in the reaction mixture within a range of from 1 to 50 mM.

9. The process for producing an α-hydroxy acid or an α-hydroxyamide as claimed in claim 1, wherein the reaction mixture contains sulfite ion.

10. A process for producing an α-hydroxy acid or an α-hydroxyamide by a microorganism or processed product thereof having nitrilase or nitrile hydratase activity, which comprises treating an aldehyde represented by the following formula (1) and prussic acid with the microorganism or processed product thereof in an aqueous medium to thereby provide a reaction mixture containing the corresponding α-hydroxy acid or α-hydroxyamide represented by formula (3), maintaining the cyanogen concentration in the reaction mixture within a range of from 0.01 to 300 mM and supplying the aldehyde to the reaction mixture in an amount of from 0.98 to 1.05 mol per mol of prussic acid:

  (1)

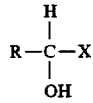  (2)

wherein R represents a substituted or unsubstituted alkyl group, a substituted or unsubstituted alkenyl group, a substituted or unsubstituted cycloalkyl group, a substituted or unsubstituted aryl group, or a substituted or unsaturated, saturated or unsaturated heterocyclic group; and X represents an amido group or carboxyl group, wherein said processed product comprises one of a ground cell, a crude enzyme, a purified enzyme, an immobilized cell or an immobilized enzyme.

11. The process for producing an α-hydroxy acid or an α-hydroxyamide as claimed in claim 10, wherein said supplying step further comprises measuring the cyanogen concentration in said reaction mixture and continuously or intermittently supplying prussic acid to the reaction mixture in such manner so as to maintain the cyanogen concentration in the reaction mixture within a range of from 0.01 to 300 mM.

12. The process for producing an α-hydroxy acid or an α-hydroxyamide as claimed in claim 11, wherein said supplying step comprises supplying an aqueous cyanide salt solution to the reaction mixture and regulating the supply rate of the aqueous cyanide salt solution so as to maintain the cyanogen concentration in the reaction mixture within a range of from 0.01 to 300 mM.

13. The process for producing an α-hydroxy acid or an α-hydroxyamide as claimed in claim 10, which comprises maintaining the cyanogen concentration in the reaction mixture within a range of from 0.1 to 100 mM.

14. The process for producing an α-hydroxy acid or an α-hydroxyamide as claimed in claim 10, which comprises maintaining the cyanogen concentration in the reaction mixture within a range of from 1 to 50 mM.

15. The process for producing an α-hydroxy acid or an α-hydroxyamide as claimed in claim 10, wherein the reaction mixture contains sulfite ion.

* * * * *